United States Patent [19]

Troutman

[11] Patent Number: 5,041,127
[45] Date of Patent: Aug. 20, 1991

[54] OFFSET POINT SURGICAL NEEDLE

[76] Inventor: Richard C. Troutman, 860 United Nations Plaza, Apt. 30A, New York, N.Y. 10017

[21] Appl. No.: 316,320
[22] Filed: Feb. 27, 1989
[51] Int. Cl.⁵ ............................................. A61B 17/32
[52] U.S. Cl. ..................................... 606/223; 223/102
[58] Field of Search ............... 606/223, 222, 225, 224, 606/226, 227; 223/102, 103, 104; 606/224, 226, 227

[56] References Cited

U.S. PATENT DOCUMENTS

| 67,545 | 8/1867 | Hodgins | 606/222 |
| 847,452 | 3/1907 | Ascue | 223/104 |
| 1,248,825 | 12/1917 | Dederer | 606/225 |
| 1,377,359 | 5/1921 | Littlejohn | 606/223 |
| 4,128,351 | 12/1978 | Kurtz et al. | 606/223 |

FOREIGN PATENT DOCUMENTS 388254  1/1924  Fed. Rep. of Germany ...... 223/102

Primary Examiner—Mickey Yu

[57] ABSTRACT

A curved surgical needle which may be helical or planar and in which the curvature may be constant or varied with the pointed end offset from the principal longitudinal axis.

10 Claims, 3 Drawing Sheets

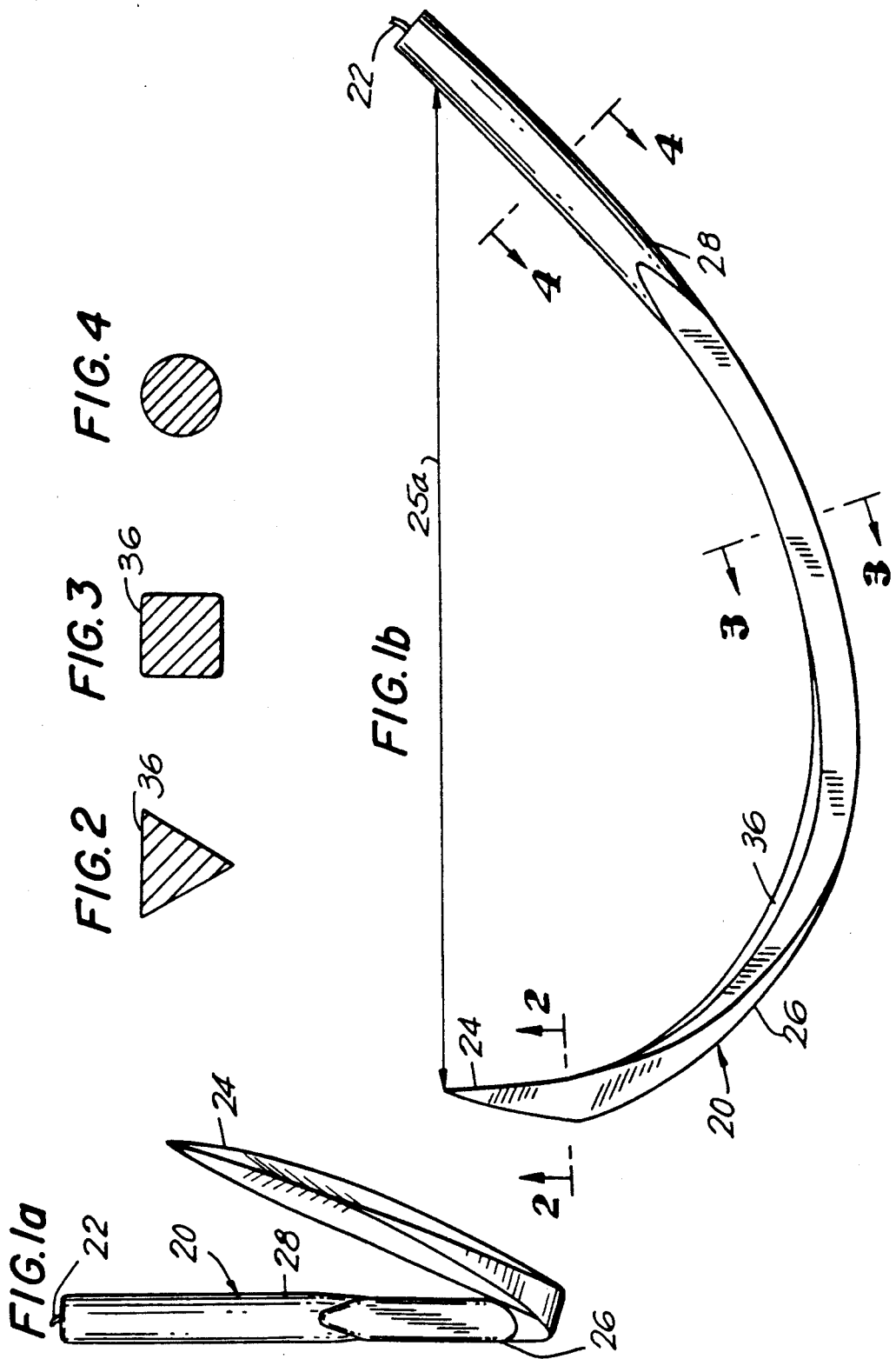

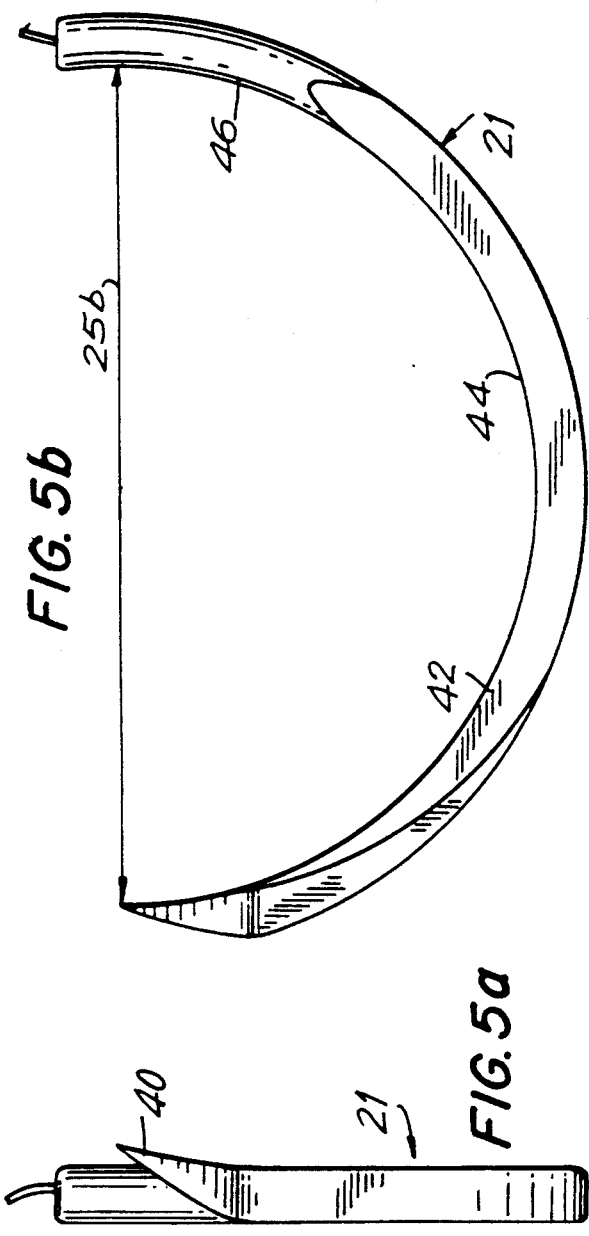
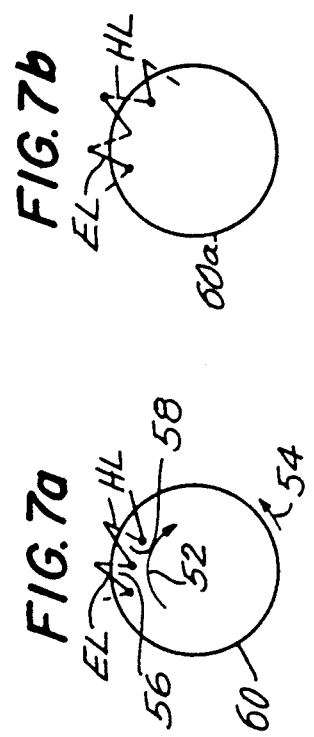
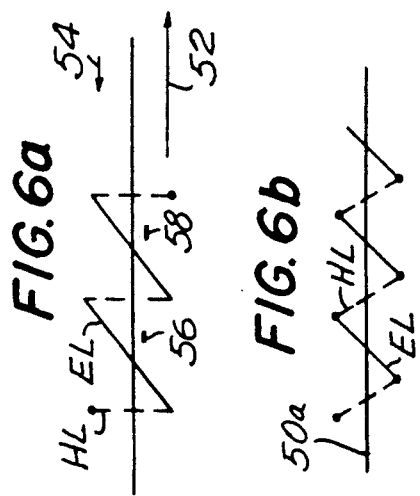

OFFSET POINT SURGICAL NEEDLE

BACKGROUND OF THE INVENTION

The present invention relates to surgical needles and more particularly to specially curved surgical needles especially advantageous for use in opthalmic microsurgery, and other microsurgery and the like.

Surgical needles can be any of a variety of shapes ranging from straight, to ski-shaped to curved. Curved needles are essential to most surgical procedures involving delicate or fine tissue to accurately locate the suture loop with a minimum of trauma to the tissue. To insert a curved needle, the surgeon must grasp the shaft of the needle with a needle holder at a point generally near the center of the needle or toward its butt to engage the tip in the tissue near the edge of the incision or wound. Then the suture is passed through the tissue and turned to pass through the tissue on the opposite side of the incision or would by a semi-rotational movement of the surgeon's fingers, wrist and forearm. The curvature of the needle helps establish for the surgeon the desired "bite" while the arcs of rotation of the surgeon's wrist and forearm or, more precisely, the arc of rotation of the needle holder held by the surgeon, establish the angulation (non-radiality) or non-angulation (radiality) of the suture across the incision or wound.

It is extremely important in certain microscopic surgery involving fragile tissue, such as in eye surgery or in anastomosis or other connection of fragile vessels or tubes, that the geometry of the path of the needle placing an appositional suture be uniform so as not to exert unequal or contrary forces parallel or tangential to the edge of the incision or would when the suture loop is formed and tied. This is important not only with individual (non-continuous) suturing but also when suturing using multiple continuous bites. For example, in a corneal transplant a continuous suture is made to define a series of isosceles triangles, so as not to induce undesirable rotative force between graft and recipient cornea.

Curved surgical needles, according to prior art construction, are curved in a single plane. As a surgeon observes them, particularly when through a vertically directed surgical microscope, and seeks to establish and maintain a precise arc of rotation for needle placement, he or she must be able to observe the location of the needle and when possible its point at all times during passage. To do this requires either that the head or visual axis be moved somewhat to one the side, impossible under a powerful microscope, or, alternatively, to tilt the plane of curvature of the needle, thereby altering the direction of penetration of the needle in the tissue.

PRIOR ART

The prior art shows various curved needles of the type to which the subject invention can be applied, such as U.S. Pat. No. 3,394,704 Dery showing a needle curved in a single plane, and to the same effect to Kurtz U.S. Pat. Nos. 2,869,550 and 3,094,123, as well as the application of myself and Walter McGregor, Ser. No. 437,419 now U.S. Pat. No. 4,524,771 incorporated herein by reference and the art cited therein.

A helical needle whose helix passes through more than 360 degrees is shown in the 1972 edition of Zentralblatt fur Chirurgie in Vol. 15 starting at page 480. The purpose here is to enable rapid closure of a large wound. The helical needle is never disengaged from the tissue being sutured and hence a surgeon there does not have to continuously grasp a suturing needle. The helical needle of said Zentralblatt curves through more than 360 degrees of helix.

SUMMARY OF THE PRESENT INVENTION

The needle in accordance with the present invention is formed so that while its curvature has one or more radii, the curve is not in one plane but, to the contrary, is at an angle to any plane positioned at right angles to an axis of curvature or, alternatively, the pointed tip is offset so that the tip is visible to a surgeon viewing the needle from above as through a surgical microscope. Additionally, any flat portion of the needle on the inside of the curve, which aids the surgeon to grasp the needle more firmly than a rounded surface, is rotated or torqued as the needle curves so that its surface always faces and is parallel to the axis of curvature. This improvement may be applied to needles of constant curvature as well as to the compound curved needle shown and claimed in my patent with Walter McGregor, supra. The angle between a body portion of the needle and a plane normal to an axis of rotation may be useful from 5 degrees to 60 degrees. In a preferred embodiment, particularly useful in opthalmic surgery, I have found angles of 15 degrees to 30 degrees most useful.

In use, a surgeon grasps the needle with the needle holder at the appropriate shaft position for that needle curvature and inserts the point into the tissue to begin the 37 bite" into the tissue on, for example, the distal side of the incision. He or she begins penetration driving the needle tip downward through the tissue while in microsurgery looking down through the microscope. The view of the needle tip and transparent corneal tissue is not blocked by the shaft of the needle or by the needle holder enabling the surgeon to precisely guide the point visually through the entire bite. As the needle is rotated to engage the opposite side of the incision, the axis of rotation of the needle holder remains parallel to the axis of curvature of the needle. The linear offset of the tip of the needle from the body of the needle permits a continuous view of the needle tip without the necessity of lateral displacement of the surgeon's head (impossible in microsurgery).

BRIEF DESCRIPTION OF THE DRAWINGS

FIG. 1a is a preferred embodiment showing a compound curved needle formed as part of a helix illustrating the offset tip in accordance with the invention;

FIG. 1b is a side view of FIG. 1a.

FIG. 2 is a cross-sectional view taken on line 2—2 of FIG. 1b;

FIG. 3 is a cross-sectional view taken on line 3—3 of FIG. 1b;

FIG. 4 is a cross-sectional view taken on line 4—4 of FIG. 1b;

FIG. 5 is an embodiment showing a constant curved needle in one plane with the alternative offset tip end;

FIG. 5b is a side view of FIG. 5a;

FIG. 6a shows a perpendicular or radially placed stitch closing a linear incision. This is to be avoided in light or fragile tissue since such a stitch induces displacement of opposing wound edges.

FIG. 6b shows the preferred "isosceles" stitch (limited movement of force) which avoids linear displacement of opposing wound margins;

FIG. 7a illustrates an undesirable continuous stitch in a circular corneal transplant comparable to the stitch in FIG. 6a and FIG. 7b illustrates the preferred continuous "isosceles" in a circular corneal transplant comparable to the stitch in FIG. 6b.

DETAILED DESCRIPTION

Figure 8:
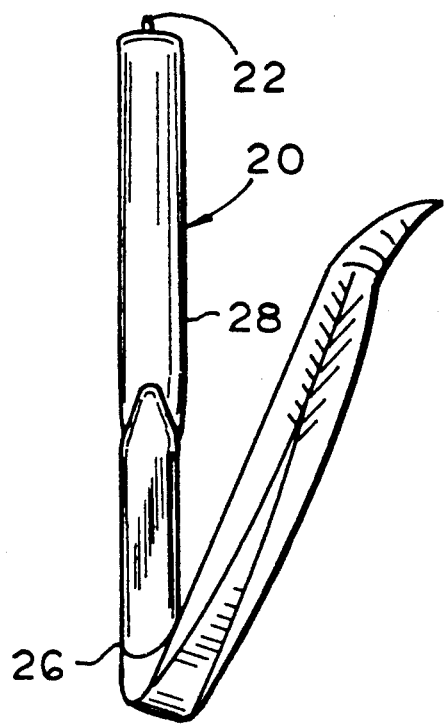
FIG. 8 is a front elevation of a needle formed as part of a helix showing an offset tip.

Referring to the drawings, FIGS. 1a and 1b show a preferred compound curved surgical needle 20 in accordance with my invention to which is secured the suture 22. The needle has a straight pointed end section 24 adjacent a curved body portion 26 with subsequent body portions 28 of reducing curvature (increasing radius of curvature). The cross-sectional shape at sections 24, 26 and 28 are shown in FIGS. 2, 3, and 4, respectively. As can be seen from FIG. 1a, the point 24 is offset from the body portion 28 and to a progressively lesser extent from body portion 26. The helical angle between the axis of the helix (axis of curvature of the helix); and a body portion is preferably 15 degrees to 30 degrees but may in some instances be as little as 5 degrees and as great as 60 degrees. In a needle in which the pointed end section 24 triangular in cross-section (FIG. 3) is 0.05" the offset would be nominally 0.025" with a range of 0.010" to 0.040". The needle may be provided with a flattened surface or face 36 which in any portion faces the axis of concavity of the curvature.

As illustrated, the needle 20 has an offset tip 24 and a body portion of successively increasing radii of curvature proceeding from tip 24 through portions 26 and 28, as more fully described in the above-mentioned Troutman et al patent incorporated herein by reference. As illustrated in FIG. 1b, the axis of curvature of each helical body portion 26,28 is co-axial although the radius of curvature is different. It should be noted that in the subject invention the offset may begin at any point along the body portions.

FIG. 5a illustrates an embodiment of my invention which incorporates the features in a needle of constant curvature. A needle of the same length but of compound curvature requires less offset than a needle of constant curvature because the chord 25a is longer than chord 25b and the grasping point of the compound curved needle is more distal from the needle point. The grasping point is normally located from the tip two-thirds the distance from tip to butt as opposed to the center as in a needle of constant curvature. Needle 21 has a tip section 40 offset from the longitudinal axis of the needle. The sections 42, 44 and 46 as illustrated are of constant radii. These sections, however, may optionally be offset in the manner illustrated for the tip 40 so that the offset is obtained by a more gradual but irregular helix.

These needles may be manufactured by any of the methods well known in the art of needle manufacture. In general, the form of the needle may be best understood by bending the wire from which the needle is formed around a mandrel whose surface contains the desired curves. For example, to make the needle 21 illustrated in FIGS. 5 and 5b a mandrel of constant diameter would be employed and the needle would be offset by being placed in a spiral curve which is cut in the mandrel and has a cross-sectional area and shape corresponding to that of the needle. The spiral would form with a plane normal to the axis of the mandrel an angle corresponding to the desired angle. In the case of the needle of FIGS. 1a, 1b, a tapered mandrel would be employed with a spiral curved as described above.

The taper would supply the decreasing radii for the several sections of needle 20. It is important that the gentler curve be placed in the wire first and then more tightly curved in the continuous operation. As clearly shown in the drawings, needles in accordance with my invention do not exceed 360 degrees and preferably are less than 180 degrees arc curvature.

FIGS. 6a and 7a illustrate radially placed continuous suturing stitches, generally not desirable for lighter or fragile tissue. The length of the external suture limb EL has a greater angle with respect to the incision 50,60 than does the internal (in the tissue) suture limb HL. This causes a larger force vector 52 of the externalized limb of stitch EL parallel to the incision 50,60 than does the force vector 54 of the perpendicular internal stitch HL. Consequently, the tissues to each side of the incision 50,60 are drawn in contrary and unequal sliding motions as illustrated by the two unequal force vectors 52 and 54 exerted by the external limb EL and the internal limb HL, respectively. This not only delays healing but also can cause a displacement at the locations 56 and 58. In the case of eye surgery this induces optical distortions of the cornea.

A stitch illustrated in FIGS. 6b and 7b in which the internal stitch HL and the external stitch EL are of equal length, form the same angle with the incision 50a, 60a and cancel out the sliding motion caused by vectors of unequal magnitude. It will be noticed that the lines of the continuous stitch form a series of isosceles triangles and that is what is meant in this patent application when the term isosceles stitch is employed. Individual radially placed or perpendicularly placed interrupted sutures such as illustrated on Plate 6-13 at p. 188 of Microsurgery of the Anterior Segment of the Eye, Vol. 1, pp. 188 through 195 can be used alternatively and their placement is similarly advantaged.

It should be obvious to one skilled in the art that in all instances direct visualization of the offset needle point during needle passage facilitates the accurate placement of both individual and continuous sutures essential to anatomical (and, in the case of eye surgery, optical) precise would apposition.

I have illustrated in FIGS. 1a and 1b a compound curved surgical needle formed as a helix in accordance with this invention. The needle of constant curvature shown in FIGS. 5a and 5b could, of course, be made helical as in the needle illustrated in FIGS. 1a and 1b. In fact, the compound curvatured needle formed as a helix to obtain the offset is my preferred embodiment. However, I have shown the needle 21 in a non-helical form to illustrate that the offset may be obtained by offsetting the point. It should be understood that an irregular helix is also within the purview of my invention. Thus, FIGS. 5a and 5b illustrate other embodiments of my invention with my preferred embodiment illustrated in FIGS. 1a, 1b.

If desired, the tip of FIG. 5a could be used with the helix of FIG. 1a as shown in FIG. 8. Also both the compound curve and constant curve can selectively be formed on a helix or in one plane to an offset tip. My preferred embodiment for the more rigid tissue encountered in corneal surgery is the compound curve needle formed on a helix to provide the offset tip.

I claim:

1. A surgical needle comprising a curved body portion terminating in one direction in a blunt end and in the other direction in a pointed end section, said pointed end section being laterally offset from said curved body portion, said curved body portion and said pointed end section together forming substantially no more than 180 degrees of arc and said pointed end section is offset 5 degrees to 60 degrees.

2. A needle according to claim 1 wherein the axis of curvature of one curved body portion is offset from the axis of curvature of another body portion 5 degrees to 60 degrees.

3. A needle in accordance with claim 1 wherein a portion of said curved body portion forms a portion of a helix formed by said portion with another body portion of said needle.

4. A needle in accordance with any of claims 1 or 3 in which a portion has a flattened surface formed on the side facing the axis of curvature of said portion.

5. A surgical needle in accordance with any of claims 1 or 3 in which said offset is 15 degrees to 30 degrees.

6. A surgical needle in accordance with any of claims 1 or 3 in which the radius of curvature of each portion is constant.

7. A surgical needle in accordance with any of claims 1 or 3, in which the radius of curvature of at least two portions differ the one from the other.

8. A surgical needle in accordance with any of claims 1 or 3, in which the radius of curvature of a portion proximal to the said pointed end is shorter than the radius of curvature of a portion more distal to said pointed end.

9. A needle according to claim 2 wherein said pointed end is offset a distance in the range of 0.010" to 0.040" at its termination.

10. A needle in accordance with claim 9 in which the length of the pointed end section is offset about 5% to 20% of the curved length of the curved body portion of said needle.

* * * * *